United States Patent [19]

Berg et al.

[11] Patent Number: 5,262,015

[45] Date of Patent: Nov. 16, 1993

[54] SEPARATION OF OCTENE-1 FROM ITS ISOMERS BY AZEOTROPIC AND EXTRACTIVE DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 24,277

[22] Filed: Feb. 26, 1993

[51] Int. Cl.⁵ .................. B01D 3/36; B01D 3/40; C07C 7/08
[52] U.S. Cl. .................. 203/57; 203/60; 203/62; 203/63; 203/64; 203/65; 585/856; 585/857; 585/862; 585/864; 585/866
[58] Field of Search .............. 203/60, 63, 62, 57, 203/65, 64; 585/856, 857, 862, 864, 866

[56] References Cited

U.S. PATENT DOCUMENTS

| | | | |
|---|---|---|---|
| 2,441,827 | 5/1948 | McKinnis | 203/60 |
| 3,312,602 | 4/1967 | Mattox et al. | 203/60 |
| 5,068,011 | 11/1991 | Lee et al. | 203/58 |
| 5,085,740 | 2/1992 | Lee et al. | 203/58 |
| 5,100,515 | 3/1992 | Lee et al. | 203/58 |

*Primary Examiner*—Wilbur Bascomb, Jr.

[57] ABSTRACT

Octene-1 is difficult to separate from several of its isomers by conventional distillation or rectification because of the closeness of their boiling points. Octene-1 can be readily separated from its close boiling isomers by azeotropic or extractive distillation. Effective agents are: for azeotropic distillation, t-amyl methyl ether; for extractive distillation, isophorone.

2 Claims, No Drawings

SEPARATION OF OCTENE-1 FROM ITS ISOMERS BY AZEOTROPIC AND EXTRACTIVE DISTILLATION

FIELD OF THE INVENTION

This to a method for separating octene-1 from its isomers using certain organic compounds as the agent in azeotropic or extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celsius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Extractive distillation typically requires the addition of an equal amount to twice as much extractive agent as the octene-1 - isomers mixture on each plate of the rectification column. The extractive agent should be heated to about the same temperature as the plate into which it is introduced. Thus, extractive distillation imposes an additional heat requirement on the column as well as somewhat larger plates.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Celsius degrees or more difference.

It is also desirable that the extractive agent be miscible with the octene-1 - isomers mixture otherwise it will form a two phase azeotrope with it and some other method of separation will have to be employed.

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The alpha olefins are useful agents to form polyolefins if they can be obtained in high purity. Many of the common sources of alpha olefins contain some of the isomers of the alpha olefins and some of these boil too close to the alpha olefin to be separated by conventional rectification. Octene-1 boils at 121.6° C. Listed below in Table 1 are the isomers of octene-1 which boil close to it.

TABLE 1

| Boiling Points of Some of the Octenes | |
|---|---|
| Isomer | B.P. |
| Octene-1 | 121.6 |
| Octene-3 | 122.3 |
| Octene-4 | 122.3 |
| 2-Methyl-2-heptene | 122.6 |
| 3-Methyl-2-heptene | 122.3 |
| 4-Methyl-3-heptene | 122.4 |
| 3-Ethyl-2-hexene | 121.1 |
| 2,3-Dimethyl-2-hexene | 121.7 |
| 2-Ethyl-1-hexene | 121.1 |

The advantage of employing an azeotropic or extractive distillation agent is shown in Table 2. Octene-1 has a relative volatility of 1.17 from its close boiling isomers and cannot be readily separated by rectification. If azeotropic or extractive distillation is employed with an agent yielding a relative volatility of 3.5, a rectification column of only fifteen actual plates will be required to produce products of 99% purity.

TABLE 2

| Effect Of Relative Volatility On The Separation Of Octene-1 From Its Isomers At 99% Purity | | | |
|---|---|---|---|
| Relative Volatility | Theoretical Plates | Actual Plates, 75% Efficiency | Actual Plates, 75% Eff., Min. Reflux |
| 1.17 | 59 | 79 | 105 |
| 1.2 | 50 | 67 | 87 |
| 1.5 | 23 | 31 | 40 |
| 2.0 | 13 | 17 | 22 |
| 3.5 | 8 | 11 | 15 |

OBJECTIVE OF THE INVENTION

The objects of this invention are to provide a process or method of azeotropic or extractive distillation that will enhance the relative volatility of octene-1 to its isomers in their separation in a rectification column. It is a further object of this invention to identify organic compounds for use as azeotropic or extractive distillation agents that are stable, can be separated from the octene isomers by rectification with relatively few plates and can be recycled with little decomposition.

SUMMARY OF THE INVENTION

The objects of this invention are provided by a process for the separation of octene-1 from its close boiling isomers which entails the use of certain organic compounds as the agent in azeotropic or extractive distillation.

DETAILED DESCRIPTION OF THE INVENTION

We have discovered that certain organic compounds will effectively increase the relative volatility between octene-1 and its close boiling isomers when employed as the agent in azeotropic or extractive distillation. Table 3 lists the compounds found to be effective azeotrope formers. They are ethyl acetate, n-propyl acetate, isoprop acetate, t-butyl acetate, n-propanol, methyl propionate, 2-pentanone, isopropyl ether, t-amyl methyl ether, methyl butyl ether, acetal and 2-methoxyethanol.

Table 4 lists the compounds found to be effective extractive distillation agents. They are dimethylsulfoxide, dimethylformamide dimethylacetamide, phenethyl alcohol, isophorone, isobornyl acetate, propylene glycol phenyl ether, ethyl valerate, ethyl caproate and ethyl salicylate.

The relative volatilities listed in Table 3 were determined in a 7.3 theoretical plate rectification column. The relative volatilities listed in Table 4 were determined in a glass vapor-liquid equilibrium still possessing about one theoretical plate.

TABLE 3

Effective Azeotrope Formers For Separating Octene-1 From Its Close Boiling Isomers

| Compounds | Relative Volatility |
|---|---|
| None | 1.17 |
| Ethyl acetate | 2.0 |
| n-Propyl acetate | 1.75 |
| Isopropyl acetate | 1.8 |
| t-Butyl acetate | 2.0 |
| n-Propanol | 1.2 |
| Methyl propionate | 1.45 |
| 2-Pentanone | 1.45 |
| Isopropyl ether | 1.75 |
| Methyl butyl ether | 2.0 |
| t-Amyl methyl ether | 2.1 |
| 2-Methoxyethanol | 1.55 |
| Acetal | 1.22 |

TABLE 4

Effective Extractive Distillation Agents For Separating Octene-1 From Its Close Boiling Isomers

| Compounds | Relative Volatility |
|---|---|
| None | 1.17 |
| Dimethylsulfoxide | 1.2 |
| Dimethylformamide | 1.21 |
| Dimethylacetamide | 1.25 |
| Phenethyl alcohol | 1.95 |
| Isophorone | 1.45 |
| Propylene glycol phenyl ether | 1.5 |
| Isobornyl acetate | 2.7 |
| Ethyl valerate | 3.0 |
| Ethyl caproate | 3.0 |
| Ethyl salicylate | 3.0 |

THE USEFULNESS OF THE INVENTION

The usefulness or utility of this invention can be demonstrated by referring to the data presented in Tables 2, 3 and 4. All of the successful agents show that octene-1 can be separated from its isomers by means of azeotropic and extractive distillation and that the ease of separation as measured by relative volatility is considerable.

WORKING EXAMPLES

Example 1

One hundred grams of 99% octene-1, 1% 2-ethyl-1-hexene and 100 grams of isophorone were charged to a vapor-liquid equilibrium still and refluxed for five hours. Analysis indicated a liquid composition of 99.39% octene-1, 0.61% isomers; a vapor composition of 99.13% octene-1, 0.87% isomers which is a relative volatility of 1.45.

Example 2

A solution comprising 100 grams of 98% octene-1 - 2% isomers mixture and 100 grams of t-amyl methyl ether was placed in the stillpot of a 7.3 theoretical plate glass perforated plate column. The column was operated at total reflux. The overhead temperature was 83° C. and the stillpot temperature was 118° C. After twelve hours of steady operation, overhead and stillpot samples were taken and analysed. The overhead composition was 47.9% octene-1, 52.1% isomers; the stillpot composition was 99.4% octene-1, 0.6% isomers which gives a relative volatility of 2.1 for a 7.3 theoretical plate column.

We claim:

1. A method for recovering octene-1 from a mixture of octene-1 and its isomers which comprises distilling a mixture of octene-1 and its isomers in the presence of an azeotrope forming agent, recovering the isomers and the azeotrope forming agent as overhead product and obtaining the octene-1 from the stillpot, wherein said azeotrope forming agent comprises a material selected from the group consisting of ethyl acetate, n-propyl acetate, isopropyl acetate, t-butyl acetate, n-propanol, methyl propionate, 2-pentanone, isopropyl ether, methyl butyl ether, t-amyl methyl ether, 2-methoxyethanol and acetal.

2. A method for recovering octene-1 from a mixture of octene-1 and its isomers which comprises distilling a mixture of octene-1 and its isomers in the presence of about one part of an extractive agent per part of octene-1 - isomers mixture, recovering the isomers as overhead product and obtaining the octene-1 and the extractive agent from the stillpot, wherein said extractive agent consists of one material selected from the group consisting of dimethylsulfoxide, dimethylformamide, dimethylacetamide, phenethyl alcohol, isophorone, propylene glycol phenyl ether, isobornyl acetate, ethyl valerate, ethyl caproate and ethyl salicylate.

* * * * *